(12) United States Patent
Greter

(10) Patent No.: US 9,131,930 B2
(45) Date of Patent: Sep. 15, 2015

(54) DEVICES FOR FILLING A MULTI-USE SYRINGE OR SINGLE-USE SYRINGE

(75) Inventor: Andy Greter, Baar (CH)

(73) Assignee: MEDMIX SYSTEMS AG, Rotkreuz (CH)

( * ) Notice: Subject to any disclaimer, the term of this patent is extended or adjusted under 35 U.S.C. 154(b) by 917 days.

(21) Appl. No.: 13/318,892

(22) PCT Filed: Dec. 17, 2009

(86) PCT No.: PCT/CH2009/000401
§ 371 (c)(1),
(2), (4) Date: Nov. 4, 2011

(87) PCT Pub. No.: WO2010/145041
PCT Pub. Date: Dec. 23, 2010

(65) Prior Publication Data
US 2012/0055580 A1 Mar. 8, 2012

(30) Foreign Application Priority Data
Jun. 19, 2009 (CH) ........................................ 962/09

(51) Int. Cl.
*B65B 1/04* (2006.01)
*A61B 17/00* (2006.01)
(Continued)

(52) U.S. Cl.
CPC ........... *A61B 17/00491* (2013.01); *A61J 1/065* (2013.01); *A61J 1/2096* (2013.01);
(Continued)

(58) Field of Classification Search
CPC ................ A61J 1/20; A61J 2001/2003; A61J 2001/2013; A61M 5/1782
USPC ........... 141/25, 27, 99; 604/87, 200; 222/325, 222/80, 82; 225/103, 97
See application file for complete search history.

(56) References Cited

U.S. PATENT DOCUMENTS

| 3,506,006 A | 4/1970 | Lange, Jr. |
| 3,892,237 A | 7/1975 | Steiner |
| 4,076,027 A | 2/1978 | Koenig |

(Continued)

FOREIGN PATENT DOCUMENTS

| GB | 467933 A | 6/1937 |
| GB | 467933 A | 6/1937 |

(Continued)

OTHER PUBLICATIONS

International Search Report of PCT/CH2009/000401 dated Apr. 7, 2010.

*Primary Examiner* — Jason K Niesz
(74) *Attorney, Agent, or Firm* — Sughrue Mion, PLLC

(57) ABSTRACT

A filling device (300) for breaking at least one ampoule (700) and for filling a syringe (600) from the ampoule is disclosed. The filling device has a base body (310), which delimits at least one hollow space (315). At the distal end, each hollow space has a removal opening, which is connected to a port (313) for the multi-use syringe. A breaking unit is designed to break the ampoule located in the hollow space. In some embodiments, the breaking unit comprises an actuating element, which is used to slide at least two ampoules onto a wedge-shaped structure, respectively, by way of a single actuating movement in the longitudinal direction, in order to apply a lateral force on the tips of the ampoules. In other embodiments, the breaking unit comprises an actuating element (320) that can be inserted in the transverse direction and acts directly on the tips of the ampoules in order to shatter or shear them off.

18 Claims, 12 Drawing Sheets

(51) Int. Cl.
*A61J 1/06* (2006.01)
*B67B 7/92* (2006.01)
*A61M 5/178* (2006.01)
*A61J 1/20* (2006.01)
*A61B 19/00* (2006.01)
*A61M 5/19* (2006.01)

(52) U.S. Cl.
CPC ........ *B67B 7/92* (2013.01); *A61B 2017/00495* (2013.01); *A61B 2019/307* (2013.01); *A61J 1/20* (2013.01); *A61J 2001/2003* (2013.01); *A61J 2001/2013* (2013.01); *A61J 2001/2027* (2013.01); *A61J 2001/2086* (2013.01); *A61M 5/1782* (2013.01); *A61M 5/19* (2013.01)

(56) References Cited

U.S. PATENT DOCUMENTS

| | | | |
|---|---|---|---|
| 5,302,358 A | * | 4/1994 | Andersen et al. ............. 422/305 |
| 6,257,474 B1 | * | 7/2001 | Jones et al. ................... 225/97 |
| 6,296,149 B1 | | 10/2001 | Long |
| 6,471,670 B1 | | 10/2002 | Enrenfels et al. |
| 6,610,033 B1 | | 8/2003 | Melanson et al. |
| 7,946,417 B2 | * | 5/2011 | Plishka et al. ................ 206/219 |
| 2003/0155381 A1 | | 8/2003 | Chan |

FOREIGN PATENT DOCUMENTS

| | | |
|---|---|---|
| GB | 984654 A | 3/1965 |
| GB | 984654 A | 3/1965 |
| WO | 98/10703 A1 | 3/1998 |
| WO | WO 98/10703 A1 | 3/1998 |
| WO | 99/17833 A1 | 4/1999 |
| WO | WO 99/17833 A1 | 4/1999 |
| WO | 99/37256 A1 | 7/1999 |
| WO | WO 99/37256 A1 | 7/1999 |
| WO | 01/41650 A1 | 6/2001 |
| WO | WO 01/41650 A1 | 6/2001 |

* cited by examiner

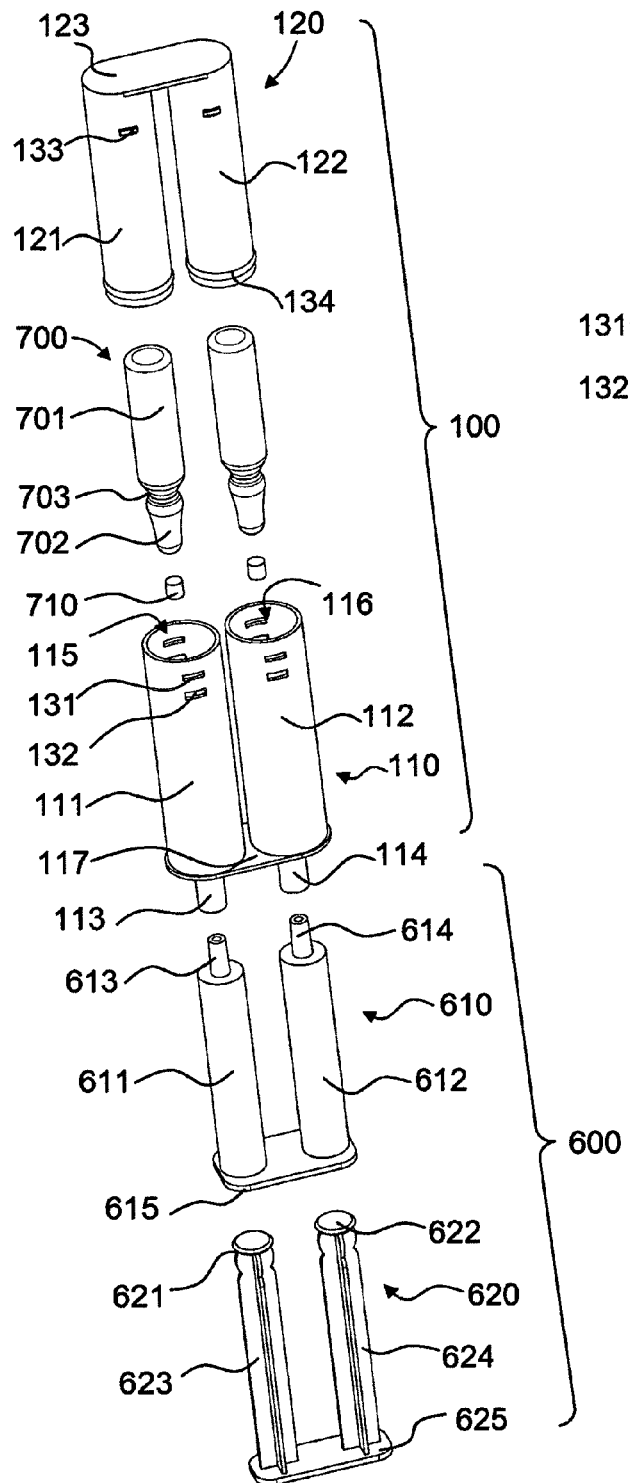
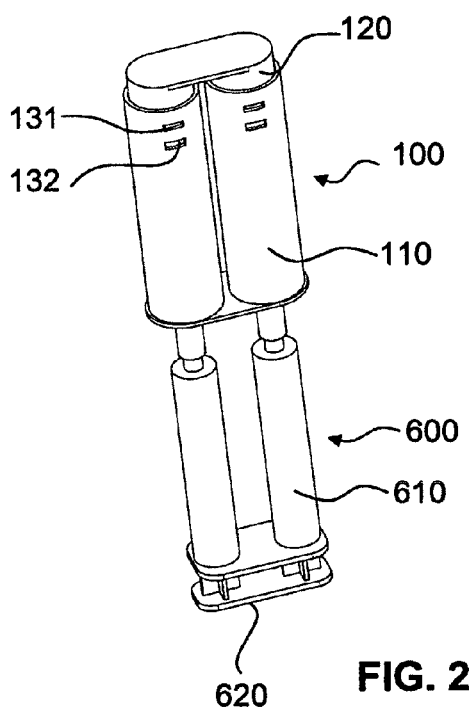
FIG. 1
FIG. 2

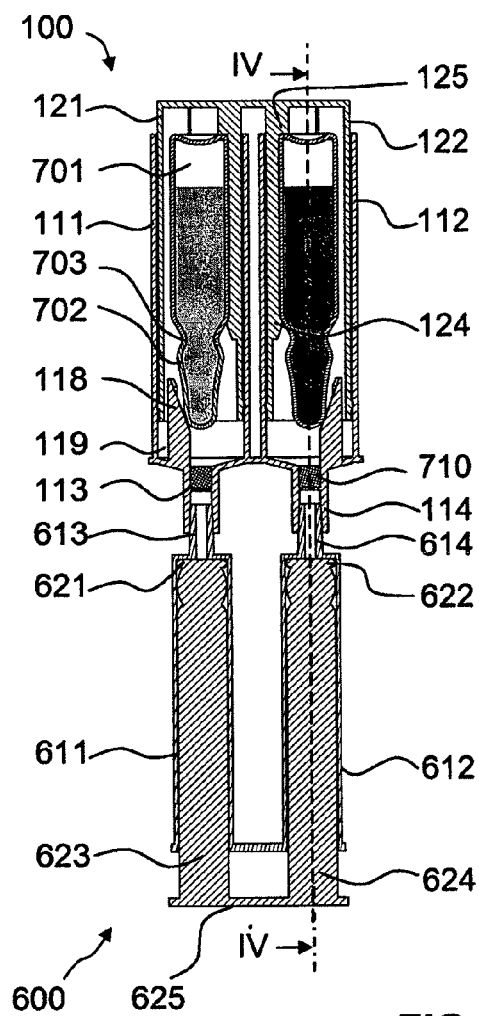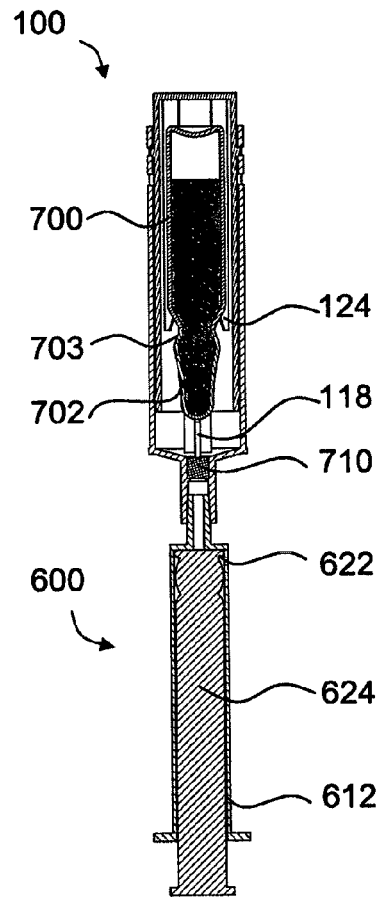
FIG. 3
FIG. 4

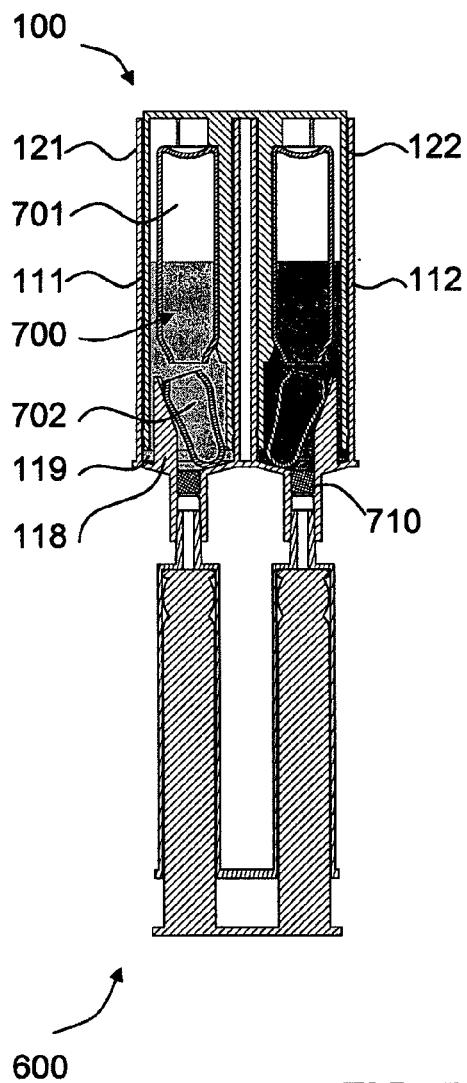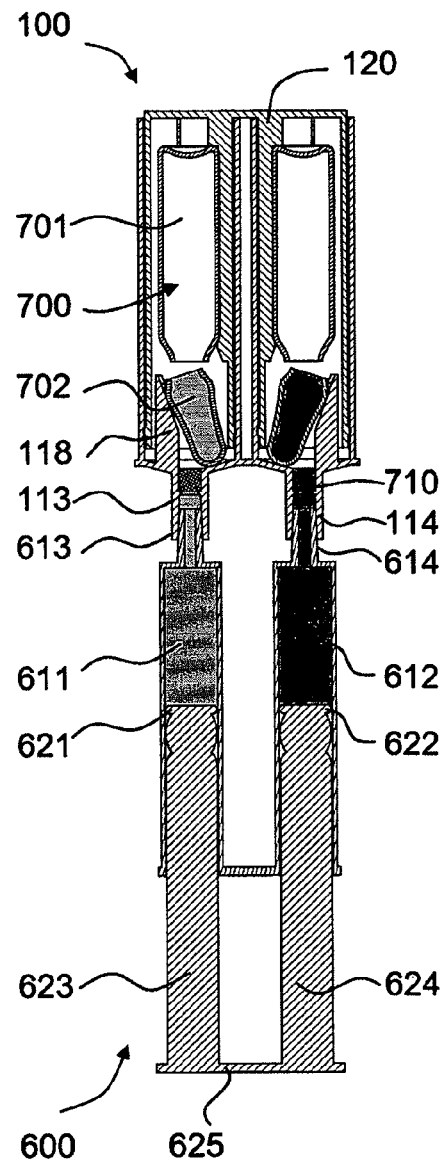
FIG. 5
FIG. 6

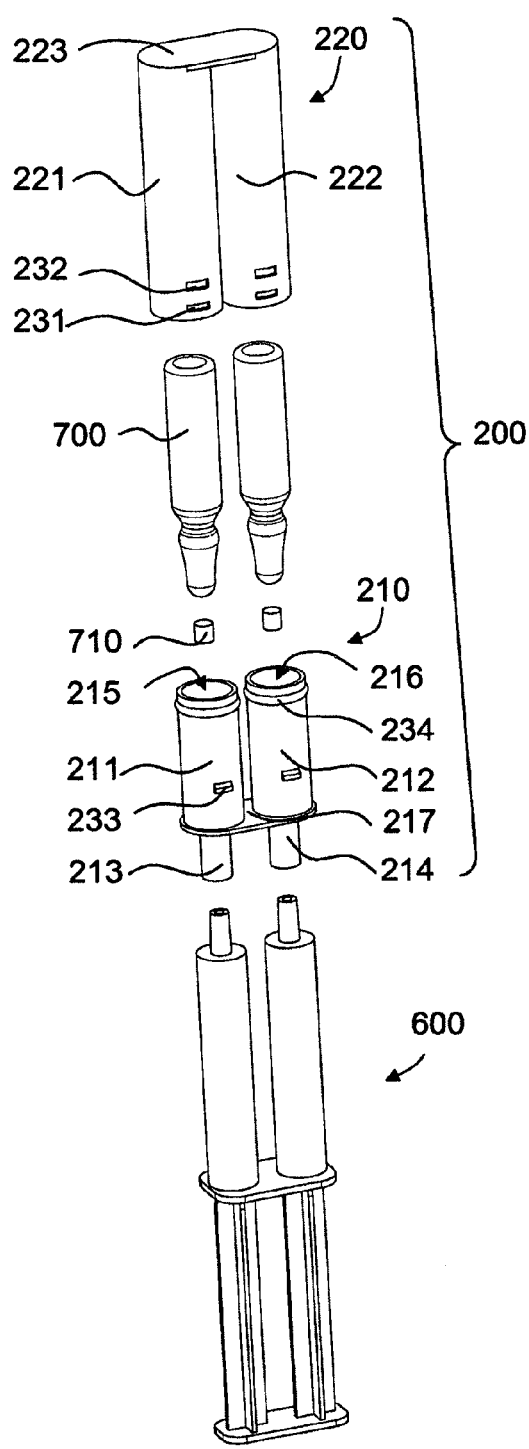
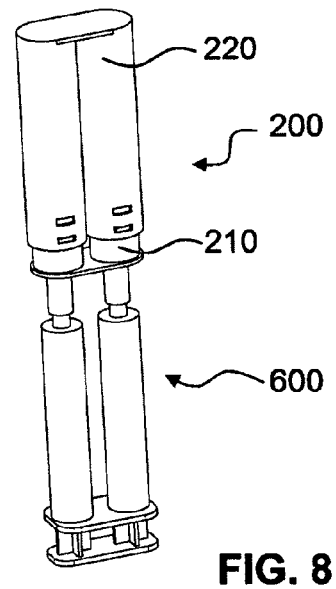
FIG. 8
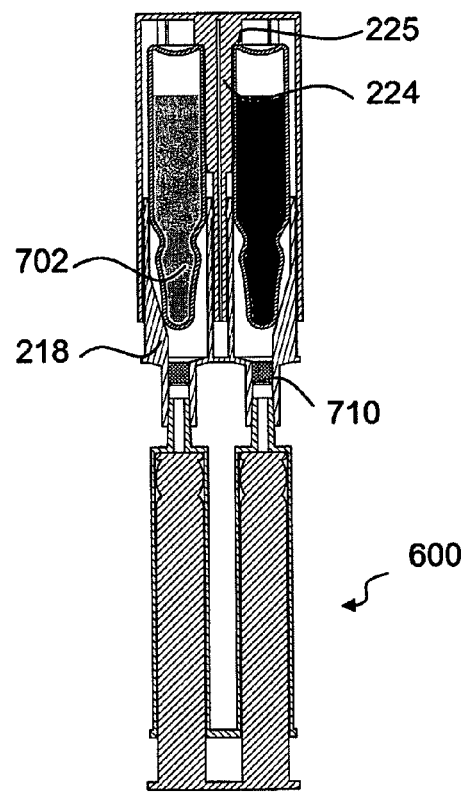
FIG. 7 FIG. 9

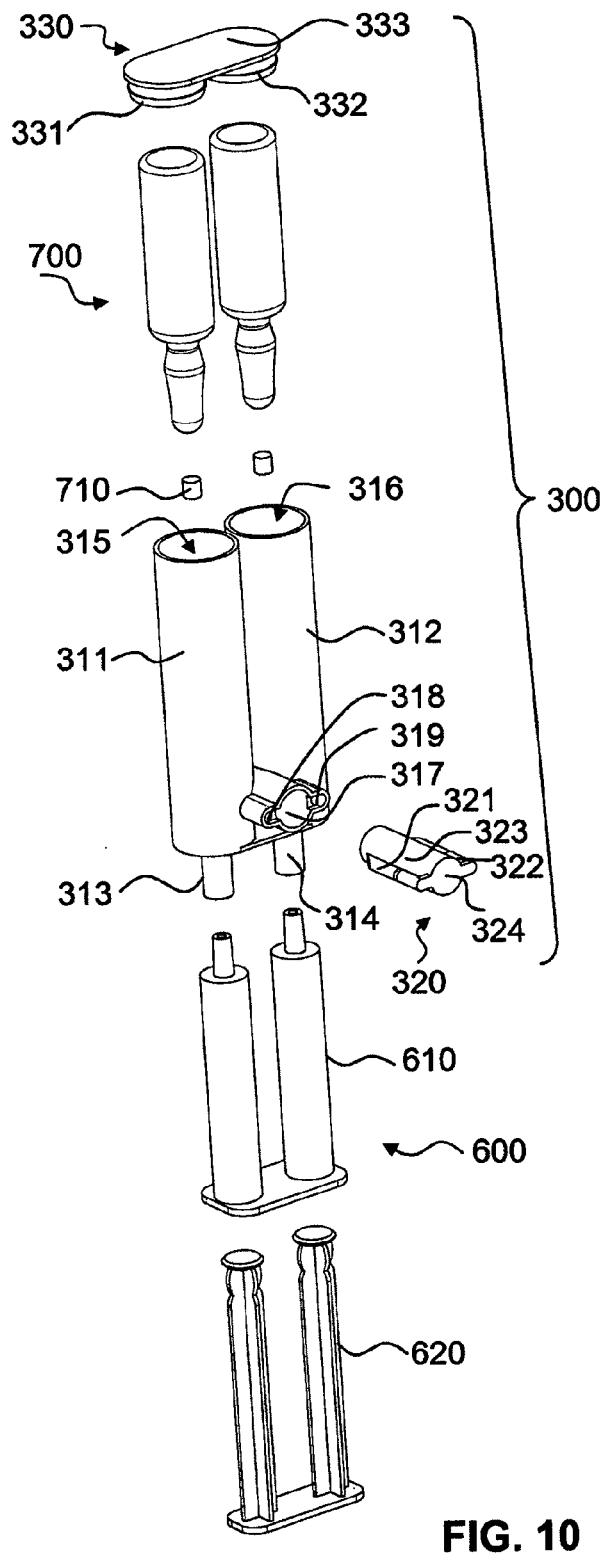
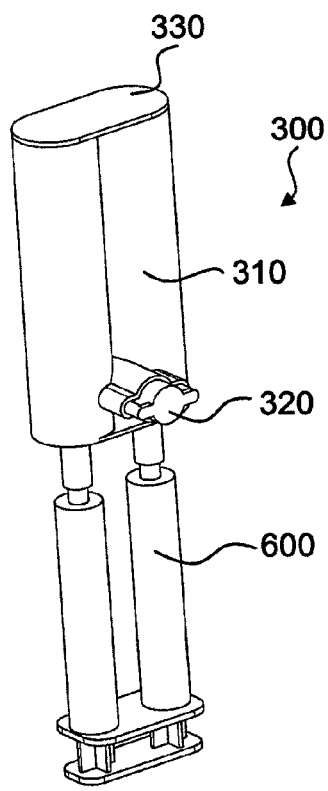
FIG. 11
FIG. 10

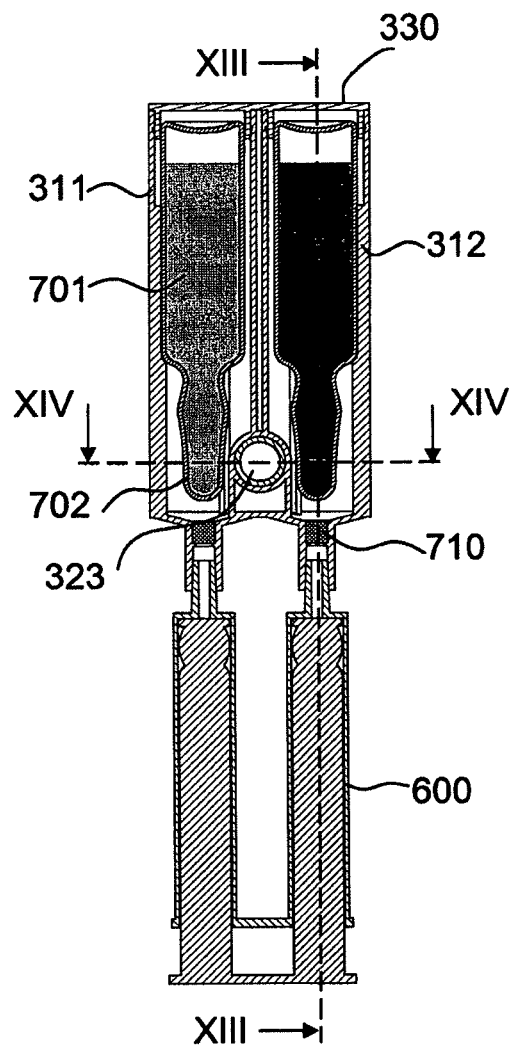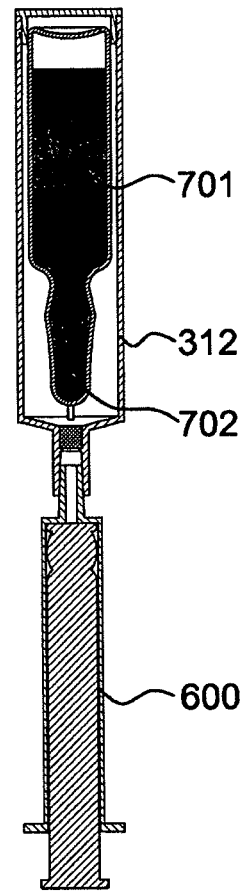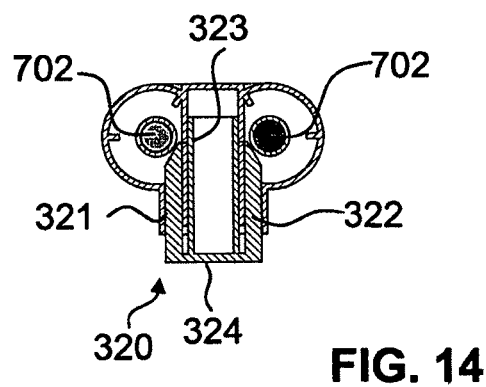
FIG. 12    FIG. 13
FIG. 14

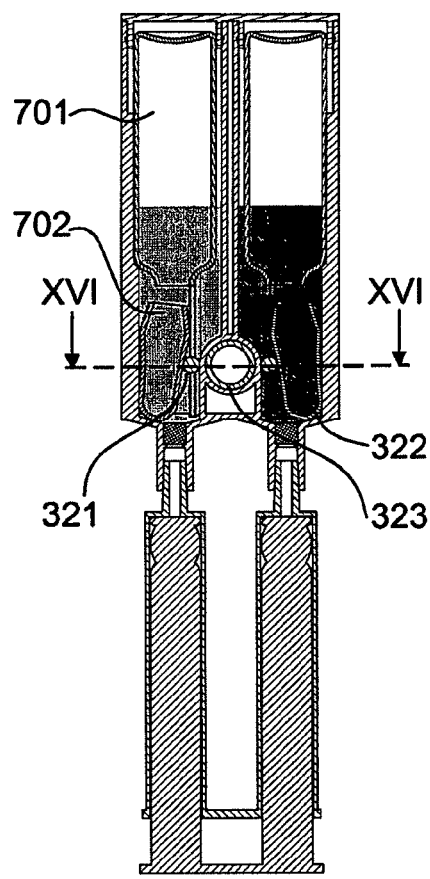
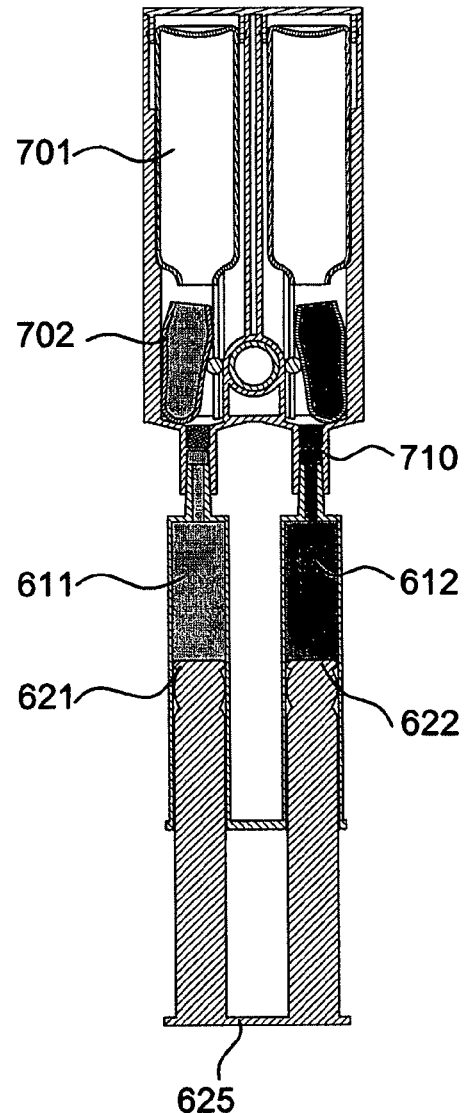
FIG. 15
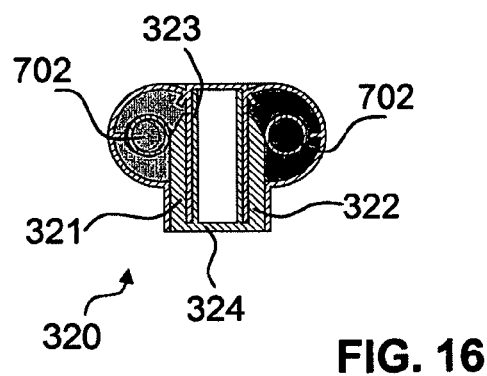
FIG. 17
FIG. 16

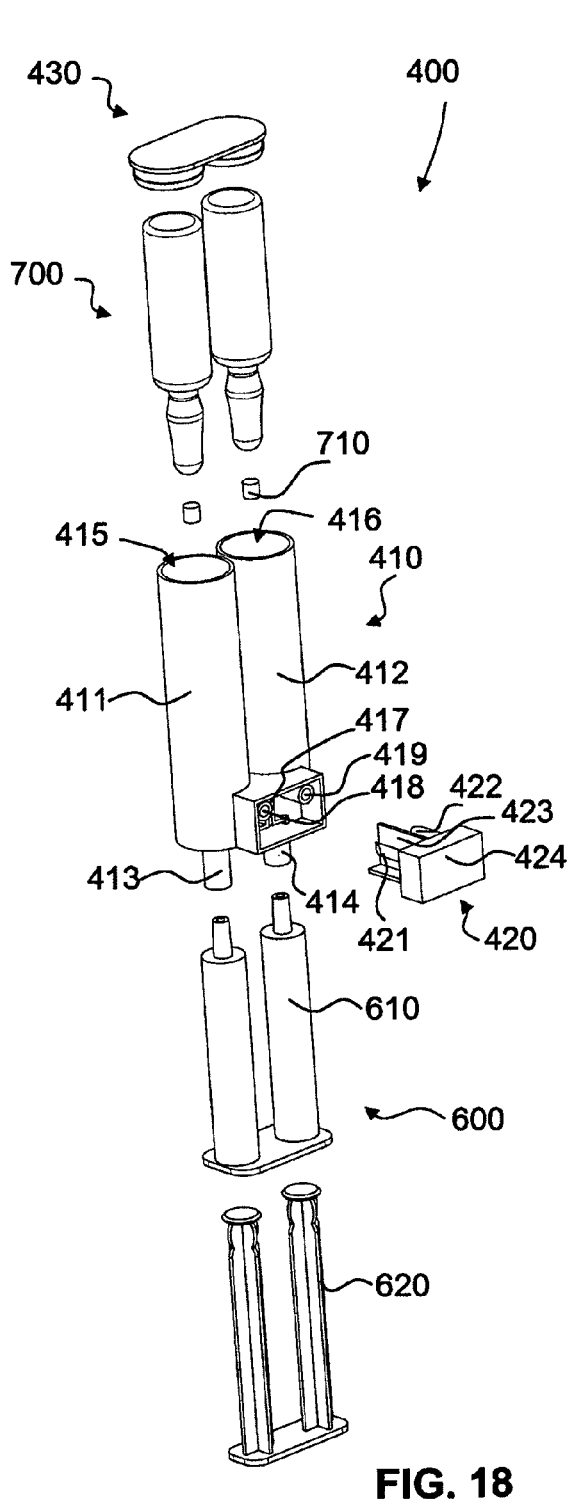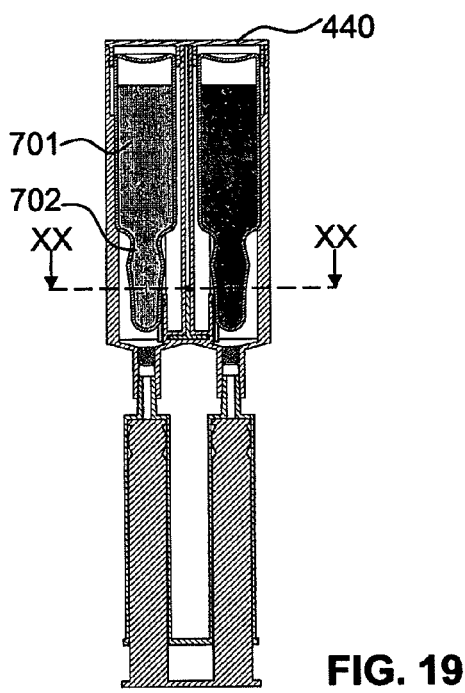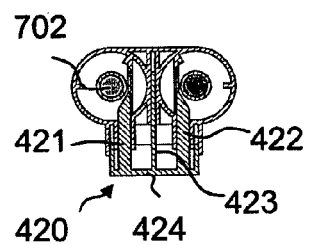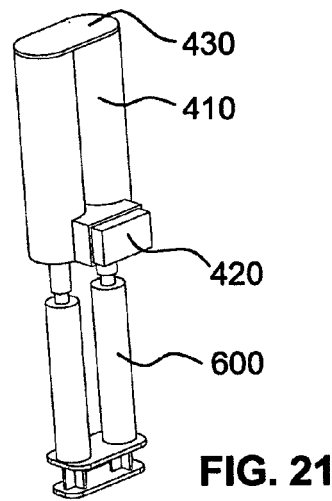
FIG. 18
FIG. 19
FIG. 20
FIG. 21

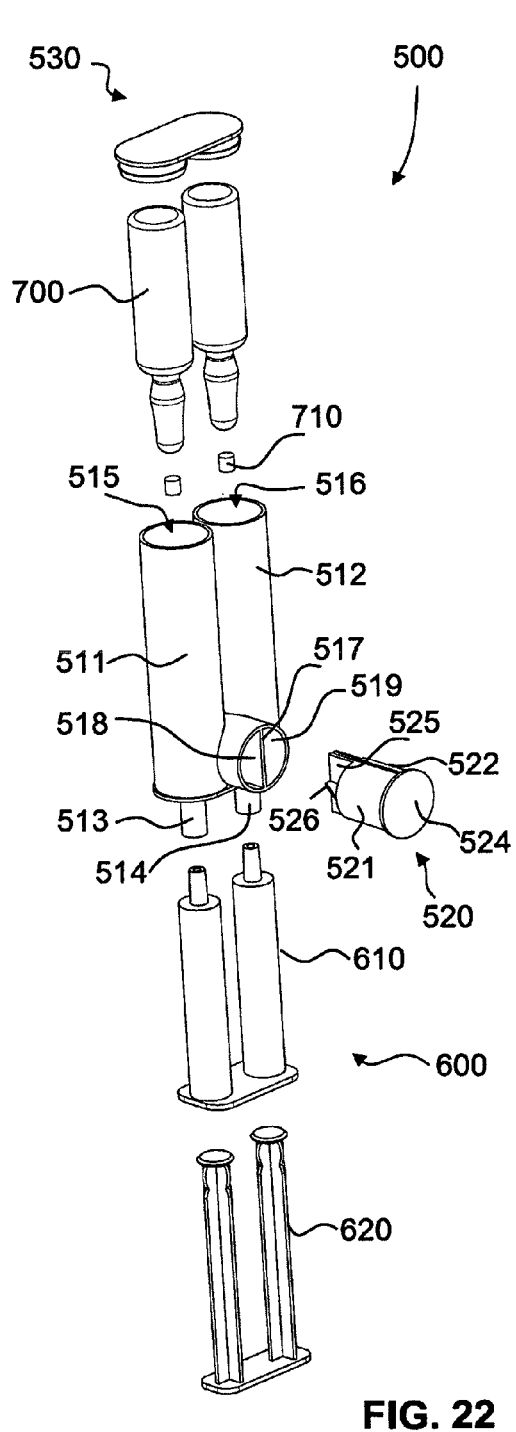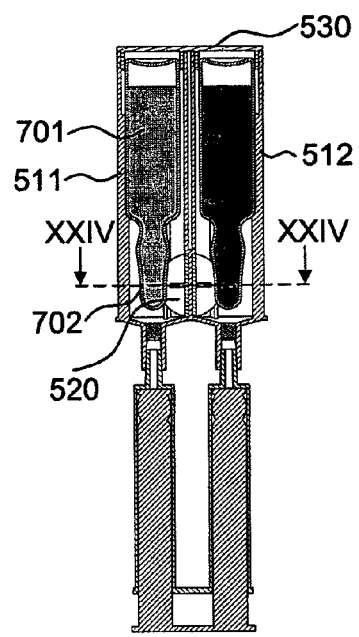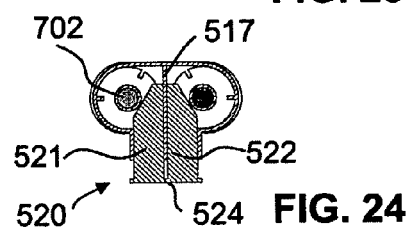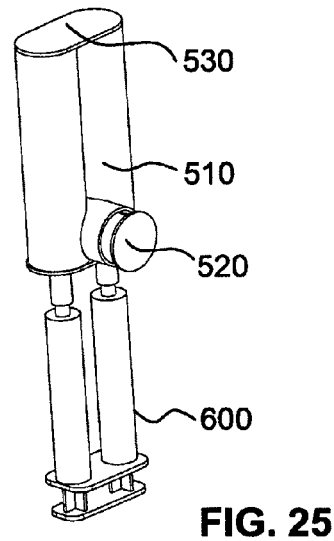
FIG. 22
FIG. 23
FIG. 24
FIG. 25

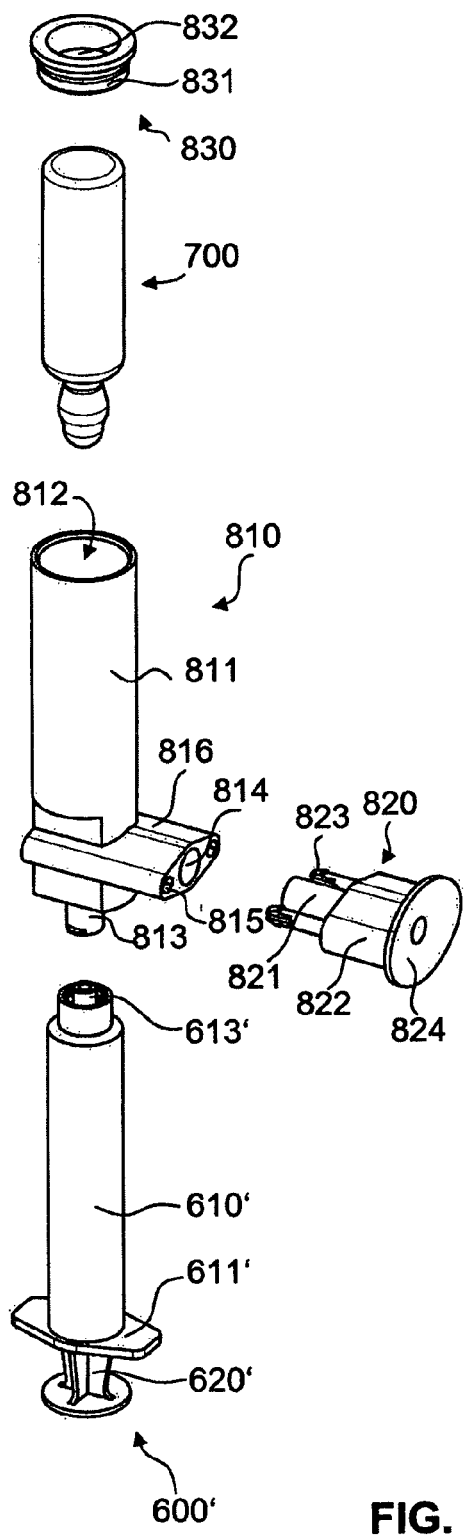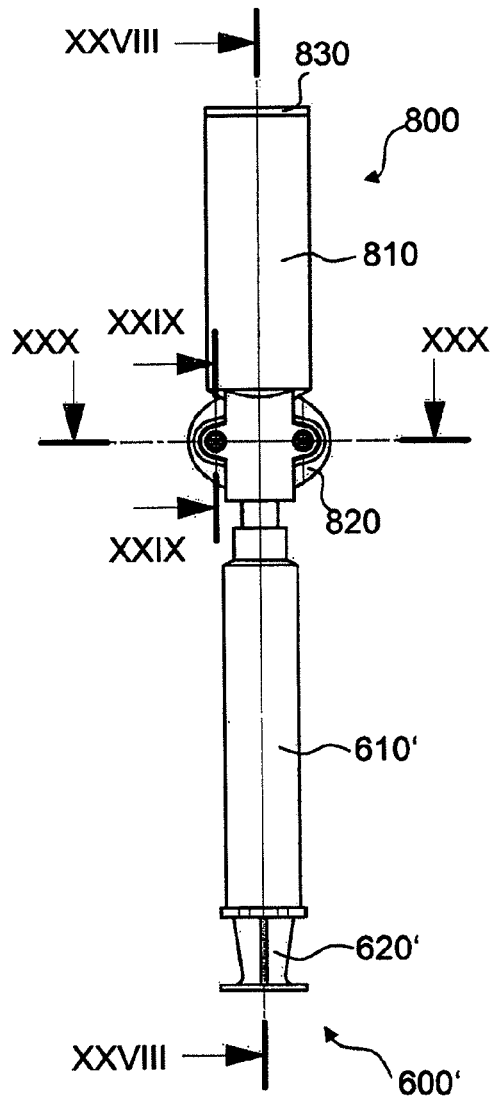
FIG. 26
FIG. 27

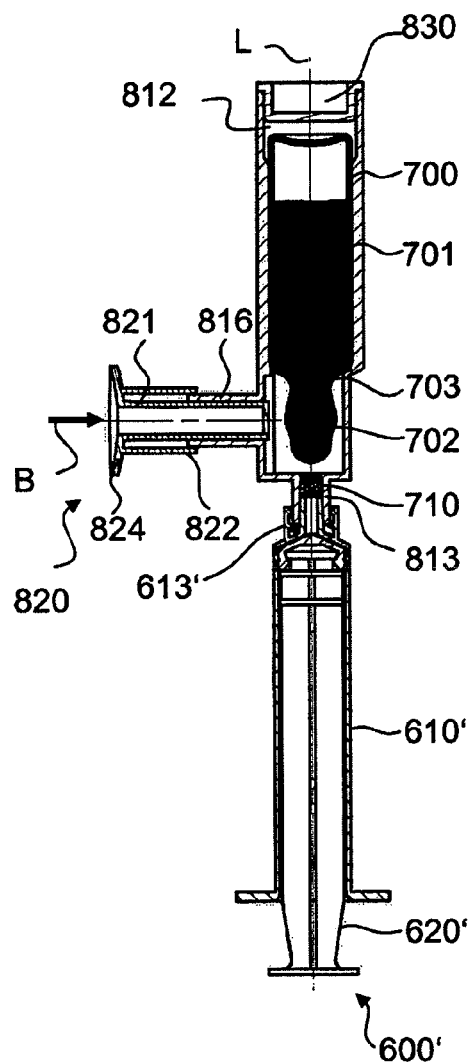
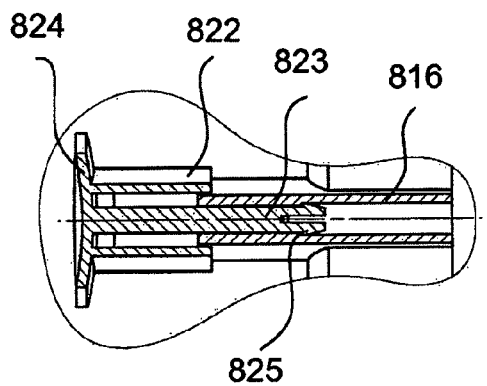
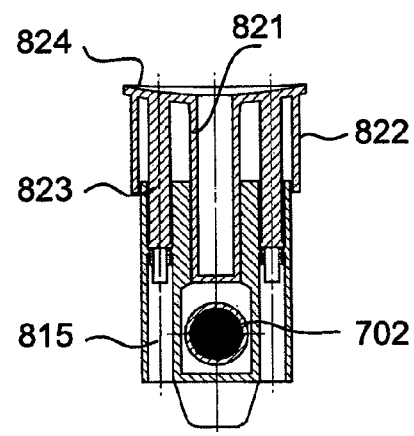
FIG. 28
FIG. 29
FIG. 30

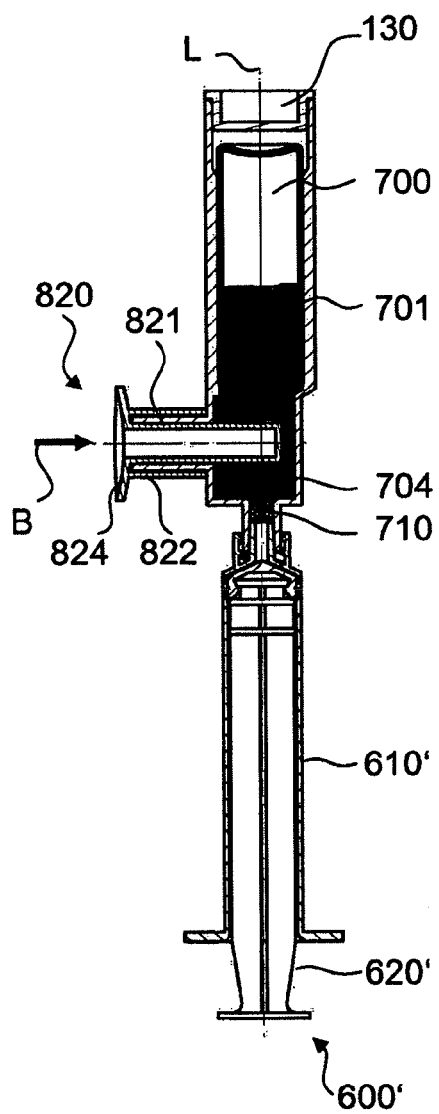
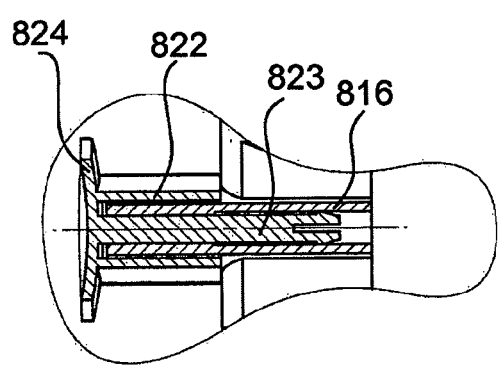
FIG. 32
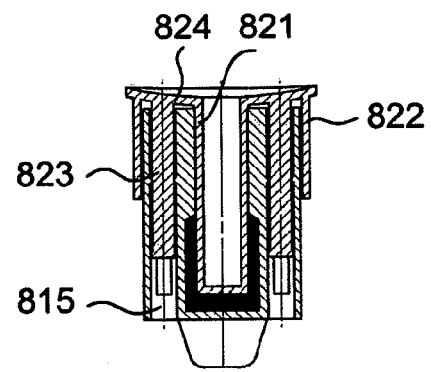
FIG. 33
FIG. 31

DEVICES FOR FILLING A MULTI-USE SYRINGE OR SINGLE-USE SYRINGE

CROSS REFERENCE TO RELATED APPLICATIONS

This application is a National Stage of International Application No. PCT/CH2009/000401 filed Dec. 17, 2009, claiming priority based on Swiss Patent Application No. 00962/09 filed Jun. 19, 2009, the contents of all of which are incorporated herein by reference in their entirety.

TECHNICAL FIELD

The present invention relates to a filling device for filling a single or multiple syringe with at least one fluid from at least one ampule.

PRIOR ART

In various applications, a task is to produce and discharge a mixture of two or more flowable components in predetermined mix ratio. One example is the production of an adhesive for technical or medical applications, for example a fibrin-based medical adhesive. Another example is the production of a bone cement from a plurality of components. There are also, for example, drugs which are produced by mixing of two or more components but are not storable in the mixed state. In this case, it is desirable to store the components separately at first and not to mix them until immediately prior to their administration. Similar tasks are also faced in other pharmaceutical or chemical systems comprising two or more components which are not stable in the mixed state.

From the prior art it is known in this connection to receive the mixing components in a double syringe and discharge them from this through a suitable mixing device. However, it is frequently problematic to store flowable substances over a lengthy period in plastic syringes, since, on the one hand, the substances can chemically react with the plastic and since, on the other hand, the danger exists that gases, in particular atmospheric oxygen, diffuse through the walls of the alter the content. This applies in particular measure to applications in the medical field, where chemical purity is of particular importance. Moreover, it is difficult with a syringe to produce sterile conditions, in particular to sterilize the syringe after it has been filled.

It is therefore known to store the mixing components separately in so-called vials, i.e. in sterilizable glass flasks which are closed at one end by a penetrable septum, and to take up the mixing components from the vials into the double syringe only shortly before application. To this end, suitable devices which enable the two syringe bodies of a double syringe to be filled simultaneously from two vials have been proposed in the prior art, for example in WO 01/41650 or in U.S. Pat. No. 6,610,033.

However, a simpler and more cost-effective option of packing a flowable substance in a sterile manner, protected from environmental influences, consists in enclosing the substance in a hermetically closed glass ampule. In order for such an ampule to be opened, it must be broken open. To this end, a predetermined breaking point, for example in the form of a constriction, can be configured on the ampule between the ampule body and the ampule tip.

Various devices for breaking a single ampule in a purposeful and neat manner are known from the prior art. For instance, GB 984,654 discloses a device for breaking a single ampule, in which the ampule is inserted in the longitudinal direction into a sleeve in which a ramp is configured. In the course of the insertion, the ramp applies a lateral force to the ampule tip, whereby the ampule tip is sheared off. After this, the ampule is removed from the sleeve and can now be emptied. With such a device, it is not possible, however, to fill a syringe directly. This is unsatisfactory from the hygienic aspect. Moreover, when the open ampule is handled, there is the danger of spillage and of injuries incurred at the sharp breaking point.

US 2003/0155381 discloses a device in which a single ampule is likewise inserted into a sleeve and is opened by being pushed axially onto a ramp. The content of the ampule is removed from the sleeve directly via a filter and a hollow needle. A similarly acting device is also disclosed in U.S. Pat. No. 3,506,006. These devices have no port for an external syringe. Even more, these devices do not allow filling of a double syringe.

In U.S. Pat. No. 4,076,027, a single ampule is shattered in a closed opening device by axial pressure upon its bottom, after which the content can be removed via an outlet of the opening device. This device too, however, is only designed to break a single ampule.

U.S. Pat. No. 6,296,149 discloses a device with which three ampules can be broken simultaneously. However, the content of all three ampules is led into a common outflow. Such a device is therefore not suitable for filling the individual syringe bodies of a multiple syringe with in each case a different component.

WO 99/37256 discloses in FIGS. 7 and 8 a bone cement mixer into which an ampule can be inserted. For opening, the ampule tip is destroyed with a laterally insertable metal pin. Because of its structure, however, this device is not suitable for transferring the content of the ampule into a syringe.

There is thus a need to define a device which is suitable for the simple and secure filling of a double or multiple syringe from two or more ampules. Even for the filling of a single syringe from a single ampule, however, known devices are only to some extent suitable, and there is need for improvements.

SUMMARY OF THE INVENTION

According to a first aspect of the invention, a device with which the filling of a multiple syringe from ampules can be performed in a neat and simple manner is provided.

A filling device for filling a multiple syringe from at least two ampules is thus proposed. The device comprises:
  a base body, which delimits at least a first and a second cavity having a proximal end and a distal end, each of the cavities defining a longitudinal direction and having at its distal end a removal opening, for removal of a fluid from the cavity;
  a first port, which communicates with the removal opening of the first cavity, and a second port, which communicates with the removal opening of the second cavity, the first and the second port being designed to interact with complementary ports of a multiple syringe; and
  a breaking unit, which is designed to break a first ampule disposed in the first cavity and a second ampule disposed in the second cavity simultaneously or successively by way of a single actuating movement.

It is thus not necessary to break the two ampules separately, but rather, with the filling device according to the invention, this can be done by way of a single movement. After this, the fluids contained in the ampules can be transferred into a connected multiple syringe separately from one another, but simultaneously.

Commercially available ampules generally have a substantially cylindrical ampule body, a closed tip and a tapered ampule neck, which is disposed between the ampule body and the tip and acts as a predetermined breaking point and at which the ampule can be broken in order to remove the content. Ampules are generally made of glass, but can also in principle consist of specific, comparatively brittle plastics.

Below, directional designations are used as follows: The distal direction denotes that direction in which a fluid is delivered from the filling device into the double syringe. The proximal direction correspondingly denotes the opposite direction.

Preferably, an ampule can respectively be inserted into the filling device, with the tip to the fore, longitudinally through the open proximal end of one of the cavities. The cavities run preferably substantially parallel to one another and define a common longitudinal direction. They preferably have a substantially cylindrical basic shape, in particular a substantially cylindrical inner contour.

The breaking unit preferably comprises an actuating element which is movable relative to the base body and which is designed to act upon the ampules disposed in the cavities by way of a single movement of the actuating element along an actuating direction. In certain embodiments, the movement of the actuating element can be made in the longitudinal direction, while in other embodiments the actuating direction runs obliquely or transversely to the longitudinal direction, in particular perpendicularly thereto. The movement of the actuating element is made from a starting position, in which the ampules are closed, into an actuating position, in which the ampules are open.

The actuating element is preferably displaceable in relation to the base body in order to break the ampules, preferably by way of a pure translatory movement. It is also conceivable, however, that the actuating element executes a more complex movement which also comprises a rotation, for example a screw movement or an arc movement, or a movement having several different motional phases, for example in order to first unlock the actuating element.

The actuating element is preferably sealed off from the base body. This prevents the fluids from possibly running out of the cavities after the breakage or from possibly intermixing in the filling device. Alternatively, the base body can also however be designed such that the ampules can be sealingly inserted in the base body, and for this purpose the base body can have a sealing structure, for example an annular taper, or a sealing element, for example a sealing ring. Preferably, each removal opening is provided with a filter in order to retain solids in the respective cavity.

In preferred embodiments, the actuating element and/or the base body have a retaining structure which prevents the actuating element from being able to be withdrawn from the actuating position back into the starting position after an actuation.

In some embodiments, the cavities run substantially parallel to one another and define a common longitudinal direction. In each of the cavities is configured a ramp, which runs at an angle to the longitudinal direction, and the actuating element is movable in relation to the base body along the longitudinal direction and is designed to press each of the ampules with their distal end against respectively one of the ramps in order to generate onto the ampules at their distal ends a force component perpendicular to the longitudinal direction. In this way, the distal end of the ampules can be sheared off. If the ampule has an ampule body and a tip, which latter is connected to the ampule body by a taper acting as the predetermined breaking point, this causes the ampule to break at the taper.

In these embodiments, the ampules are preferably held in the actuating element. To this end, the actuating element has a first and a second holding region in order respectively to hold an ampule by its proximal end, in particular by friction forces. In particular, the ampules may be plugged into the holding regions with their proximal ends. In some embodiments, the actuating element, in particular the holding regions with respectively an ampule held therein, can be inserted into the cavities along the longitudinal direction in order to push the ampules onto the ramps. In other embodiments, the actuating element can be pushed onto the base body, so that the actuating element, in a pushed-on state, at least partially surrounds the base body.

On the base body and on the actuating element, latching means are preferably configured, which latching means, at least in an end position in which the actuating element has reached a distal end position, effect a latching connection between the base body and the actuating element. The latching means, moreover, preferably effect a releasable latching connection also in a starting position in which the ampules are still intact, in order thus to provide a defined starting position. The latching means are preferably configured such that, at least in the starting position, they allow movement of the actuating element in the distal direction but prevent movement in the proximal direction.

In other embodiments, the actuating element can be inserted into the cavities along an actuating direction running obliquely or transversely to the longitudinal direction, so that the actuating element applies a force component, acting perpendicularly to the longitudinal direction, to a distal end region of each of the ampules. To this end, the actuating element can have at least two mutually connected, parallelly arranged breaking structures (in particular bolts), which can be inserted into the cavities through lateral openings of the base body. The breaking structures are preferably sealed off from the base body. They preferably respectively have a free end, on which an angular face, running obliquely to the actuating direction, is respectively configured. The breaking structures hence apply to the distal ends of the ampules a force which has a component acting both perpendicularly to the longitudinal direction and perpendicularly to the actuating direction. However, the breaking structures can also press directly along their direction of insertion against the distal end region of each of the ampules and can thus shear off or shatter this end region in the course of the insertion. In particular, the breaking structures can respectively be of blunt (for example flat or rounded) or tapered configuration at their end which is insertable into the cavity.

The actuating element preferably comprises a guide region, which can be inserted into a complementary guide structure of the base body in order to guide the actuating element on the base body. Hence the lateral openings of the base body, through which the breaking structures are inserted, do not need to take sole charge of the guidance, which makes them easier to seal. In particular, the guide structure can take the form of a further opening on the base body, into which the guide region is insertable. Preferably, this opening does not however open out into one of the cavities for the ampules.

The invention additionally relates to the combination of a filling device defined above and a multiple syringe, in particular a double syringe, wherein the multiple syringe comprises:

at least a first and a second syringe body having a cylindrical wall region, a cover wall, an outlet disposed in the cover wall, and a port communicating with the outlet;

at least a first and a second syringe plunger, each of the syringe plungers being sealingly displaceable in the cylindrical wall region of one of the syringe bodies;

an actuating element, which mutually connects the first and the second syringe plunger in order to move both syringe plungers simultaneously;

each of the ports of the syringe bodies being connectable to a complementary port of the filling device.

According to a further aspect of the invention, a method for filling a multiple syringe having at least two syringe bodies from at least two ampules is provided, having the following steps:

insertion of the ampules into a filling device having a breaking unit;

breaking of the ampules by the breaking unit by way of a single actuating movement; and take-up of a fluid from each of the ampules into respectively one of the syringe bodies of the multiple syringe.

According to a further aspect, the present invention provides a device with which also a single receptacle, in particular a single syringe, can be filled easily and securely from at least one ampule.

A filling device for filling a receptacle with a fluid from at least one ampule is thus proposed. The device comprises a base body which forms at least a first cavity extending along a longitudinal direction and having a proximal end and a distal end. The base body is designed to receive an ampule, at least by its distal end, sealingly in the first cavity. In the region of the distal end of the cavity, said base body has a removal opening, for removal of a fluid from the cavity, as well as a port, which communicates with the removal opening and is designed to interact with a complementary connecting piece of a receptacle. The filling device further comprises an opening device, which is designed to open an ampule disposed in the first cavity. The opening device comprises an actuating element, insertable into the base body along an actuating direction in order to shear off or shatter a distal end region of an ampule arranged properly in the base body, the actuating direction running at an angle (obliquely or transversely) to the longitudinal direction. The actuating element thus generates a force component, acting transversely to the longitudinal direction, onto a distal end region of the ampule. In particular, the actuating direction preferably runs at an angle of substantially 90° to the longitudinal direction. The actuation is realized from a starting position into an inserted actuating position.

Preferably, the actuating element can be inserted into the base body along the actuating direction by a pure translatory movement, in order to open the ampule. The insertion movement of the actuating element can also however run along an arc-shaped path, though the center axis of the arc movement (i.e. the pivot axis in the case of a pivot movement) preferably does not coincide with the central center axis of the cavity in which the ampule is accommodated. The actuating element is preferably insertable into an distal end region of the cavity adjacent to the opening, the end region being closer to the distal end of the cavity having the removal opening than to the proximal end of the cavity.

The actuating element is preferably sealed off from the base body. In preferred embodiments, the base body has in the direction of the cavity an actuating opening and the actuating element has a breaking structure which can be inserted through the actuating opening into the cavity of the base body in order to open the ampule. In order to seal off the actuating element from the base body, it is then advantageous if a seal is configured in the region of the actuating opening between the breaking structure and the base body.

The actuating element can be designed to shatter the distal end region of the ampule. Hence fluid which is present in the ampule tip can also be removed. To this end, the actuating element can have a breaking structure, which, when the actuating element is inserted into the base body, moves into the cavity, in particular the distal end region thereof, in such a way that it shatters an end region of an ampule held properly in the base body. The breaking structure, in the inserted state, can project substantially centrally into the cavity.

In other embodiments, the actuating element can be designed to shear off the distal end region of the ampule. To this end, the actuating element can once again have a breaking structure which can be inserted by one end into the cavity, in particular into the distal end region thereof. At this end of the breaking structure, an angular face, running obliquely to the actuating direction, can be configured, in order to apply to an end region of an ampule held properly in the base body a shearing force acting at an angle to the longitudinal direction and at an angle to the actuating direction.

In order to improve the guidance of the actuating element, an additional guide structure for the actuating element can be configured on the base body in order to guide the actuating element on the base body. In particular, the guide structure can have at least one guide opening, running parallel to the actuating opening, and the actuating element can have a guide region complementary thereto, for example a guide pin, which can be inserted into the guide opening in order to guide the actuating element on the base body. Preferably, the guide opening does not open out into the cavity for the ampule.

On the actuating element and/or on the base body can be configured a retaining structure, which prevents the actuating element in its actuating position from being pulled back out. To this end, at least one springy or resilient latch boss can be present, for example, on the actuating element or on the base body, which latch boss, in the inserted state, interacts with an edge of the respectively other element and thus effects a latching connection.

In some embodiments, the filling device is used to fill a single receptacle, in particular a single syringe, with a single fluid from a single ampule. In this case, the base body delimits precisely one cavity for the reception of precisely one ampule.

As already indicated above, such a filling device can also however be used to fill a plurality of receptacles, for example the syringe bodies of a double or multiple syringe. To this end, the base body additionally delimits at least a second cavity having a proximal end and a distal end, the base body is designed to receive at least a second ampule, at least by its distal end, sealingly in the second cavity, and the base body has a second removal opening, for removal of a fluid from the second cavity. The first and the second cavity then run substantially parallel to one another and define a common longitudinal direction.

The actuating element then preferably comprises at least two mutually connected, parallelly arranged breaking structures, which can be inserted into actuating openings of the base body along the actuating direction in order to shear off or shatter distal end regions of ampules disposed in the base body. Hence at least two ampules can be opened by way of a single actuating movement. Alternatively, at least two separate actuating elements, which can be separately actuated in order to respectively break an ampule, may also however be present.

Furthermore, the present invention also relates to a combination of a filling device of said type and a syringe, wherein the syringe comprises:
- at least a first syringe body having a cylindrical wall region, a cover wall, an outlet disposed in the cover wall, and a connecting piece communicating with the outlet;
- at least a first syringe plunger, which is sealingly displaceable in the cylindrical wall region of the syringe body;
- the connecting piece of the syringe body being connectable to a complementary port of the filling device.

BRIEF DESCRIPTION OF THE DRAWINGS

Preferred embodiments of the invention are described below with reference to the drawings, which serve merely for illustrative purposes and should not be interpreted as limiting the invention.

First Embodiment

FIG. 1 shows an exploded view of a filling device with breaking unit according to a first embodiment, together with a double syringe;

FIG. 2 shows a view of the filling device and double syringe of FIG. 1 in the assembled state, prior to actuation of the breaking unit;

FIG. 3 shows a central longitudinal section through the filling device of FIG. 1 in the assembled state, prior to actuation of the breaking unit;

FIG. 4 shows a longitudinal section in the plane IV-IV of FIG. 3;

FIG. 5 shows a central longitudinal section through the filling device of FIG. 1 in the assembled state, following actuation of the breaking unit but prior to filling of the double syringe; and FIG. 6 shows a central longitudinal section through the filling device of FIG. 1 in the assembled state, following filling of the double syringe.

Second Embodiment

FIG. 7 shows an exploded view of a filling device with breaking unit according to a second embodiment, together with a double syringe;

FIG. 8 shows a view of the filling device and double syringe of FIG. 7 in the assembled state, prior to actuation of the breaking unit; and FIG. 9 shows a central longitudinal section through the filling device of FIG. 7 in the assembled state, prior to actuation of the breaking unit.

Third Embodiment

FIG. 10 shows an exploded view of a filling device with breaking unit according to a third embodiment, together with a double syringe;

FIG. 11 shows a view of the filling device and double syringe of FIG. 10 in the assembled state, prior to actuation of the breaking unit;

FIG. 12 shows a central longitudinal section through the filling device of FIG. 10 in the assembled state, prior to actuation of the breaking unit;

FIG. 13 shows a longitudinal section in the plane XIII-XIII of FIG. 12;

FIG. 14 shows a cross section in the plane XIV-XIV of FIG. 12;

FIG. 15 shows a central longitudinal section through the filling device of FIG. 10 in the assembled state, following actuation of the breaking unit but prior to filling of the double syringe;

FIG. 16 shows a longitudinal section in the plane XVI-XVI of FIG. 12; and

FIG. 17 shows a central longitudinal section through the filling device of FIG. 10 in the assembled state, following filling of the double syringe.

Fourth Embodiment

FIG. 18 shows an exploded view of a filling device with breaking unit according to a fourth embodiment, together with a double syringe;

FIG. 19 shows a central longitudinal section through the filling device of FIG. 18 in the assembled state, prior to actuation of the breaking unit;

FIG. 20 shows a cross section in the plane XX-XX of FIG. 19; and

FIG. 21 shows a view of the filling device and double syringe of FIG. 18 in the assembled state, prior to actuation of the breaking unit.

Fifth Embodiment

FIG. 22 shows an exploded view of a filling device with breaking unit according to a fifth embodiment, together with a double syringe;

FIG. 23 shows a central longitudinal section through the filling device of FIG. 22 in the assembled state, prior to actuation of the breaking unit;

FIG. 24 shows a cross section in the plane XX-XX of FIG. 23; and

FIG. 25 shows a view of the filling device and double syringe of FIG. 22 in the assembled state, prior to actuation of the breaking unit.

Sixth Embodiment

FIG. 26 shows an exploded view of a filling device with breaking unit according to a sixth embodiment, together with a single syringe;

FIG. 27 shows a view of the filling device of FIG. 26, from behind;

FIG. 28 shows a central longitudinal section in the plane XXVIII-XXVIII through the filling device of FIG. 26, prior to actuation of the breaking unit;

FIG. 29 shows a partial view of a longitudinal section through the filling device of FIG. 26 in the plane XXIX-XXIX;

FIG. 30 shows a cross section of the filling device of FIG. 26 in the plane XXX-XXX;

FIG. 31 shows a central longitudinal section of the filling device, following actuation of the breaking unit;

FIG. 32 shows a partial view as in FIG. 29, following actuation of the breaking unit; and FIG. 33 shows a cross section as in FIG. 30, following actuation of the breaking unit.

DESCRIPTION OF PREFERRED EMBODIMENTS

First Embodiment

In FIGS. 1 to 6, a first embodiment of a filling device 100 according to the invention, with a double syringe 600 connected thereto, is shown.

The double syringe 600 comprises a main body 610 having a first and a second cylindrical syringe body 611, 612 arranged in parallel. On the front ends of the syringe bodies, connecting pieces 613, 614, in the present example in the form of male luer ports, are configured. At their rear end, the two syringe bodies 611, 612 are connected by a connecting plate 615. Into the main body 610 can be inserted a double plunger 620. The latter comprises two syringe plungers 621, 622, which are connected to one another by two parallel plunger rods 623, 624 and an actuating flange 625 connecting the plunger rods.

The filling device comprises a base body 110 having two parallel running receiving regions 111, 112 of cylindrical basic shape, which are mutually connected at their distal ends by a connecting plate 117. Each of the two receiving regions 111, 112 delimits a cavity 115, 116. At the distal end of the base body 110 are configured two ports 113, 114 for connection to the double syringe. These ports can be coded, i.e. they can be marked differently or configured such that the double syringe 600 can be fastened to the ports 113, 114 only in predetermined orientation, for example by way of different shape or dimensions. In the present example, both ports, however, are configured as identical female luer ports. Each of the ports 113, 114 is connected to one of the cavities 115, 116 by a removal opening. In the respective removal opening is respectively inserted a cylindrical filter 710 (FIG. 3), which is used to retain solids in the cavity. This can be in the form of a sintered filter, for example, which can be pressed into the opening. As can be seen, in particular, from FIG. 3, inside each of the two receiving regions 111, 112 is respectively configured a wedge-shaped structure 118, which is arranged laterally offset relative to the respective longitudinal axis and forms at its proximal end a narrow angular face or ramp, which slopes in the distal direction toward the longitudinal axis. The wedge-shaped structure 118 is arranged at a distance from the shell wall of the respective receiving region, so that a partially annular gap 119 remains between the shell wall and the wedge-shaped structure 118.

The filling device 100 additionally comprises an actuating element 120, which is designed to hold two ampules 700 and insert them into the base body 110 in order to break the ampules. To this end, the actuating element 120 has two cylindrical, parallelly arranged holding regions 121, 122, which at their proximal ends are connected by a connecting plate 123. As can be seen, in particular, in FIGS. 3 and 4, on the inner shell surface of the hollow cylindrical holding regions 121, 122 are configured holding structures 124 in the form of at least three longitudinally running ribs, which at their distal end have inwardly projecting, beveled retaining bosses. When an ampule 700 is inserted by its ampule body 701 into one of the holding regions, the holding regions yield in the radial direction to the point that the ampule body can slide through between the retaining bosses. Once the ampule is wholly inserted, it butts at the proximal end against a stop 125. In this position, the retaining bosses end up in the region of the taper 703 of the ampule 700 and thereby hold the latter in the inserted position.

The two cylindrical holding regions 121, 122 of the actuating element 120 can be inserted, with the ampules accommodated therein, longitudinally into the cavities 115, 116 of the base body 110. A seal is here configured between the base body 110 and the actuating element 120, in that a sealing ring 134 is respectively configured on the outer side of the cylindrical shell surfaces of the holding regions 121, 122, close to the respective distal end. This sealing ring 134 bears sealingly against the inner shell surface of the receiving regions 111, 112 of the base body and thus produces a liquid-tight seal.

Close to the proximal end of the actuating element 120, a latch boss 133, which is beveled in the distal direction, is respectively configured on the outer side of the shell surfaces of the two holding regions 121, 122. On the base body 110, two latch openings 131, 132, arranged at a distance apart along the longitudinal direction, are respectively configured close to the proximal end of the two receiving regions 111, 112. Once the actuating element 120 has been inserted sufficiently far into the base body 110, each of the latch bosses 133 engages with the respective first latch opening 131. The actuating element 120 is hereby temporarily prevented from being pushed further into the base body 110. This is the position which is represented in FIGS. 2 to 4. In this position, the tip 702 of each of the two ampules bears respectively in a force-free manner against one of the angular faces of the wedge-shaped structures or is located at a short distance from this angular face.

If a sufficiently large force is now applied in the distal direction to the actuating element 120, the latch boss 133, by virtue of its bevel, slides out of the first latch opening 131 and the actuating element 120 is pushed further into the base body 110. The ampules are hereupon pressed with their tips 702 against the angular faces of the wedge-shaped structures 118. This generates a force component which acts perpendicularly to the longitudinal direction and thereby causes the tips of the ampules, at the tapers 703 acting as predetermined breaking points, to be broken off from the ampule body 701. The cylindrical shell wall of the respective holding region 121, 122 of the actuating element 120 hereupon slides with its distal end into the corresponding partially annular gap 119. The latch boss 133 slides into the second latch opening 132 and effects a permanent latching of the actuating element 120 to the base body 110, which latching prevents withdrawal of the actuating element 120. This is the situation of FIG. 5.

Since the ampules are now broken open, the content of the ampules can empty into the respective cavity and can be received with the double syringe 600 into the two syringe bodies 611, 612, in that the syringe plungers 621, 622 are retracted by means of the plunger rods 623, 624 and the actuating flange 625. This is illustrated in FIG. 6.

Should glass splinters have been formed in the breaking of the ampules, then they are retained by the filters 710 in the respective cavities and cannot make their way into the syringe bodies 611, 612.

Second Embodiment

A second embodiment of a filling device is represented in FIGS. 7 to 9. The same parts are here denoted with the same reference numerals as in the first embodiment. The filling device 200 once again comprises a base body 210 and an actuating element 220. The base body 210 once again comprises two parallel, cylindrical receiving regions 211, 212, which are connected to one another by a connecting plate 217. Once again, the receiving regions 211, 212 delimit two cavities 215, 216, which through corresponding removal openings open out into ports 213, 214. The actuating element 220 once again comprises two parallel running, cylindrical holding regions 221, 222, which are once again connected by a connecting plate 223. Inside the holding regions 221, 222, holding structures 224 and a stop 225 are once again configured in order to respectively receive and hold an ampule 700 in each holding region. The holding structures 224 are once again configured as longitudinally running ribs. These are configured shorter than in the first embodiment, however, and have no retaining boss at their distal end.

Unlike in the first embodiment, the actuating element in the second embodiment cannot be inserted into the base body, but is pushed onto the base body, so that the cylindrical side wall regions of the holding regions 221, 222 surround the receiving regions 211, 212 of the base body in their proximal region. Here a seal is once again configured between the base body 210 and the actuating element 220. In this embodiment, the seal is formed by a sealing ring 234 respectively on the outer shell surface of each receiving region 211, 212. In this embodiment too, a two-stage latching connection exists between the base body 210 and the actuating element 220. To this end, a latch boss 233 is respectively configured on the outer shell surfaces of the receiving regions 211, 212 of the base body 210, which latch boss interacts with latch openings 231, 232 in the shell surfaces of the holding regions 221, 222 of the actuating element 220.

The principle of operation of this device is substantially the same as that of the first embodiment. Once again, a wedge-shaped structure 218 is respectively configured inside the base body 210 in each of the receiving regions 211, 212, which wedge-shaped structure forms an angular face or ramp onto which the tip 702 of the respective ampule is pushed in order to laterally shear off the tip. Since the actuating element 220 in this embodiment, however, is pushed onto the base body 210 instead of being inserted into it, a partially annular gap between the wedge-shaped structure 218 and the respective shell wall can here be dispensed with.

In both embodiments, of course, a number of modifications are possible. It is thus possible, for example, to hold the ampules displaceably in the base body 110 or 210 instead of in the actuating element 120 or 220, so that the actuating element is merely used to advance the ampules along the longitudinal direction. It is also conceivable to configure a seal directly between the base body and the ampules, so that a seal between the base body and the actuating element can be dispensed with. The latching connections can be differently configured, for example with spring tongues, or can also be dispensed with in simplified embodiments. The wedge-shaped elements 118, 218 can be of different length, so that the ampules are not broken simultaneously, but directly one after the other. In this way, the user perceives whether both ampules have actually been broken and requires less force for the breaking. Many other modifications are possible.

Third Embodiment

In FIGS. 10 to 17, a third embodiment of a filling device is represented. In this embodiment, the actuation is realized not in the longitudinal direction, but in the transverse direction. Here, once again, a force component is generated which acts perpendicularly to the longitudinal direction in order to break off the ampule tips from the ampule bodies.

The filling device 300 once again comprises a base body 310 having two parallel running receiving regions 311, 312, which delimit two cavities 315, 316 and open out into ports 313, 314. Two ampules 700 are fully insertable into the receiving regions. The base body 310 can then be sealingly closed by a cap 330 having two stoppers 331, 332, which are connected by a cover plate 333. On each of the two receiving regions 311, 312, in the region of its distal end, there is respectively configured a lateral opening 318, 319. Between these openings is a hollow cylindrical guide structure 317, the cylinder axis of which runs in the transverse direction and which likewise is laterally open. Into the guide structure 317 and the openings 318, 319, an actuating element 320 can be laterally inserted. This comprises a push-button-like actuating region 324, a cylindrical guide region 323, which is configured complementary to the guide structure 317, and two parallel bolts 321, 322, which act as breaking structures and can be inserted through the lateral openings 318, 319 into the cavities 315, 316.

FIGS. 11 to 14 here illustrate a starting position in which, though the actuating element 320 is inserted in the base body 310, it has not yet been actuated to open the ampules. On the free ends of the bolts 321, 322 are configured angular faces or ramps, which run at an angle to the transverse direction. These ramps bear in a force-free manner against the tips 702 of the ampules 700 or have a certain short distance to these tips. FIGS. 15 and 16 illustrate how the actuating element 320 has been pushed in further in order to break the ampules. The ramps of the bolts 321, 322 have now laterally pressed away the tips 702 of the ampules 700 in a direction running transversely to the actuating direction and to the longitudinal direction. The ampules are thereby broken in the region of their taper 703 acting as predetermined breaking points. As is illustrated in FIG. 17, the liquid present in the ampules can now be received into the two syringe bodies of the double syringe 600.

In order to prevent the liquid from running out, a seal is here respectively configured between the bolts 321, 322 and the receiving regions 311, 312, in that the bolts 321, 322 sit snugly in the openings 318, 319. Since the diameter of the bolts is comparatively small, no further particular measures are necessary for the sealing. The guidance of the actuating element 320 on the base body 310, by contrast, is realized independently of the seal, primarily by the interaction of the guide region 323 with the guide structure 317. The different requirements of guidance and seal are thus met by separate structures.

Fourth Embodiment

A fourth embodiment is illustrated in FIGS. 18 to 21. The filling device 400 of this embodiment is in principle structured similarly to the filling device of the third embodiment (base body 410, receiving regions 411, 412, ports 413, 414, cavities 415, 416, transversely insertable actuating element 420, cap 430). Once again, lateral openings 418, 419 are present, through which bolts 421, 422 of the actuating element 420 can be inserted. As in the third embodiment, these are provided at their ends with ramps and thereby act upon the ampules in the same way as in the third embodiment. The actuating element 420 is guided, by a T-shaped guide region 423, in a corresponding complementary guide structure 417 on the base body 410. The actuating region 424 is here of rectangular shape and is received, in the end position, in a corresponding rectangular frame of the base body 410.

Fifth Embodiment

A fifth embodiment is illustrated in FIGS. 22 to 25. The filling device 500 of this embodiment is also in principle structured similarly to that of the third embodiment (base body 510, receiving regions 511, 512, ports 513, 514, cavities 515, 516, transversely insertable actuating element 520, cap 530). The lateral openings 518, 519 for the insertion of the actuating element 520 are here of semicylindrical construction. The actuating element has correspondingly semicylindrical bolts 521, 522, connected by a circular actuating region 524, and at their ends a narrow ramp 526 is respectively configured on a guide plate 525 extending the interfaces between the semicylinders. Between the bolts and the guide plates is found a narrow, straight slit, which, upon the insertion of the actuating element, receives within it a partition 517 separating the two openings 518, 519. The bolts 521, 522 are once again guided sealingly in the base body 510. In this embodiment, a separate guide structure is dispensed with.

Sixth Embodiment

A sixth embodiment is illustrated in FIGS. 26 to 33. The filling device 800 is here designed to fill a single syringe 600' from a single ampule 700.

The filling device 800 comprises a base body 810, which has a cylindrical receiving region 811 for the ampule 700. The base body 810 delimits with the receiving region 811 a cavity 812 for the reception of the ampule. With its cylinder axis, the cavity defines a longitudinal direction. At its proximal end, the cavity 812 can be closed by a cap 830 having a sealing skirt 831, insertable into the cavity 812, and having a cover wall 832. The cavity opens out at its distal end into an outlet, in which a filter 710 (FIG. 28) is disposed and which communicates with a port 813 for the syringe 600'. The port is once again configured as a female luer port, but can also, however, be configured as a male luer port or in some other form.

In the region of the distal end of the receiving region 811, a guide structure 816 is configured on the side of the base body 810. This guide structure has a lateral opening 814, which opens into a distal end region of the cavity 812. Running parallel thereto are two bores or guide openings 815, which have no connection to the cavity 812.

Into the base body 810 can be inserted an actuating element 820. This has a breaking structure in the form of a cylindrical bolt 821, which with its free end can be introduced into the lateral opening 814 of the base body. At this end, the bolt 821 is configured flat, but can also however be of sloping or tapered, in particular pointed, configuration. Running parallel to the bolt 821 are two guide pins 823, which are insertable into the two guide openings 815. At their front end, the guide pins are longitudinally slotted and have forward beveled latch bosses, which in the inserted state engage in corresponding steps in the guide openings 815 (FIG. 29).

In order to fill the syringe 600' from the ampule 700, the ampule 700 is inserted into the cavity 812 of the filling device. After this, the cavity is closed with the cap 830. The syringe 600' is now connected by its connecting piece 613' to the port 813 of the filling device. This is the situation depicted in FIGS. 28-30.

In order to open the ampule, the actuating element 820 is now inserted. The free end of the bolt 821 thereby makes its way into the distal end region of the cavity 812, in which the ampule tip 702 is located, and shatters the latter. In this movement, the actuating element 820 is additionally guided by the guide pins 823. Instead of shattering the ampule tip, it is also conceivable to shear off the ampule tip by the use of an angular face or ramp. Since the ampule tip is shattered, it becomes possible, however, also to remove the content of the ampule tip, while, if the ampule tip is merely sheared off, a remnant of the content remains in the tip. The content of the ampule now pours out into the cavity and can be transported through the removal opening into the syringe 600'. To this end, the syringe body 610' is held in the usual manner with the aid of the holding flange 611' while the syringe plunger 620' is drawn out of the syringe body 610'.

From the above described illustrative embodiments, it is evident that a large number of modifications can be made without departing from the scope of the invention. For instance, in the first five embodiments bolts without angular faces can be used and a force can be applied to the tips of the ampules directly in the actuating direction. In these embodiments, the bolts can have different lengths in order to break the ampules successively instead of simultaneously. The bolts can be insertable, instead of in the transverse direction, also in a direction running at a different angle to the longitudinal direction, preferably, however, within the range −45° to +45°. Numerous further modifications are possible.

In all embodiments, the base body is preferably produced in one piece from plastic. The actuating element, too, is preferably produced in one piece. A very cost-effective production, which allows single use of the device, is thereby possible.

LIST OF REFERENCE SYMBOLS

First Embodiment

100 filling device
110 base body
111 first receiving region
112 second receiving region
113 first port
114 second port
115 first cavity
116 second cavity
117 connecting plate
118 wedge-shaped structure
119 gap
120 actuating element
121 first holding region
122 second holding region
123 connecting plate
124 holding structure
125 stop
131 first latch opening
132 second latch opening
133 latch boss
134 sealing ring Second Embodiment

200 filling device
210 base body
211 first receiving region
212 second receiving region
213 first port
214 second port
215 first cavity
216 second cavity
217 connecting plate
218 ramp
220 actuating element
221 first holding region
222 second holding region
223 connecting plate
224 holding structure
225 stop
231 first latch opening
232 second latch opening
233 latch boss
234 sealing ring Third Embodiment

300 filling device
310 base body
311 first receiving region
312 second receiving region 313 first port
314 second port
315 first cavity
316 second cavity
317 guide structure
318 lateral opening
319 lateral opening
320 actuating element
321 first bolt
322 second bolt
323 guide region
324 actuating region
330 cap
331 first stopper
332 second stopper
333 cover plate Fourth Embodiment 400 filling device
410 base body
411 first receiving region
412 second receiving region
413 first port
414 second port
415 first cavity
416 second cavity
417 guide structure
418 lateral opening
419 lateral opening
420 actuating element
421 first bolt
422 second bolt
423 guide region
424 actuating region
430 cap Fifth Embodiment 500 filling device
510 base body
511 first receiving region
512 second receiving region
513 first port
514 second port
515 first cavity
516 second cavity
517 opening structure
518 lateral opening
519 lateral opening
520 actuating element
521 first bolt
522 second bolt
524 actuating region
525 guide plate
526 ramp
530 cap First to Fifth Embodiment 600 double syringe
610 main body
611 first syringe body
612 second syringe body
613 first connecting piece
614 second connecting piece
615 connecting plate 620 double plunger
621 first plunger
622 second plunger
623 first plunger rod
624 second plunger rod
625 actuating flange Sixth Embodiment 600' single syringe
610' main body
611' holding flange
613' connecting piece
620' syringe plunger
800 filling device
810 base body
811 receiving region
812 cavity
813 port
814 lateral opening
815 guide opening
816 guide structure
820 actuating element
821 bolt
822 skirt
823 guide pin
824 actuating surface
830 cap
831 stopper
832 cover surface All Embodiments 700 ampule
701 ampule body
702 ampule tip
703 taper
710 filter

The invention claimed is:
1. A filling device for filling a multiple syringe from at least two ampules, the filling device comprising:
a base body delimiting at least a first and a second cavity, each of the cavities having a proximal end and a distal end, each of the cavities defining a longitudinal direction and having at its distal end a removal opening, for removal of a fluid from the cavity;
a first port communicating with the removal opening of the first cavity, and a second port communicating with the removal opening of the second cavity, the first and the second port being configured to interact with complementary connecting pieces of a multiple syringe; and
a breaking unit, which is configured to break a first ampule disposed in the first cavity and a second ampule disposed in the second cavity simultaneously or successively by way of a single actuating movement,
wherein the breaking unit comprises an actuating element which is movable relative to the base body and which is configured to act upon the ampules disposed in the cavities by way of a single movement of the actuating element along an actuating direction,
wherein the actuating element is adapted to be advanced into the cavities along an actuating direction running obliquely or transversely to the longitudinal direction in order to apply a force component, acting perpendicularly to the longitudinal direction, to a distal end region of each of the ampules, and wherein the actuating element comprises at least two mutually connected, parallelly arranged breaking structures, which are adapted to be advanced into the cavities through lateral openings of the base body.

2. The filling device as claimed in claim 1, wherein the cavities run substantially parallel to one another and define a common longitudinal direction.

3. The filling device as claimed in claim 1, wherein the actuating element is displaceable in relation to the base body in order to break the ampules.

4. The filling device as claimed in claim 1, wherein the breaking structures have free ends, on which an angular face, running obliquely to the actuating direction, is respectively configured.

5. The filling device as claimed in claim 1, wherein the actuating element has a guide region, which is adapted to be inserted into a complementary guide structure of the base body in order to guide the actuating element on the base body.

6. A filling device for filling a receptacle with a fluid from at least one ampule,
the filling device comprising a base body which forms at least a first cavity extending along a longitudinal direction and having a proximal end and a distal end, the base body being configured to receive an ampule, at least by its distal end, sealingly in the first cavity,
wherein the base body has a removal opening, for removal of a fluid from the cavity,
wherein the base body has a port, which communicates with the removal opening of the base body and is configured to interact with a complementary connecting piece of a receptacle,
and wherein the filling device additionally comprises an opening device, which is configured to open an ampule disposed in the first cavity,
the opening device comprising an actuating element which is adapted to be advanced into the base body along an actuating direction in order to shear off or shatter a distal end region of an ampule arranged properly in the base body, the actuating direction running at an angle to the longitudinal direction,
wherein an additional guide structure for the actuating element is configured on the base body, in order to guide the actuating element on the base body,
wherein the guide structure has a guide opening, and
wherein the actuating element has a guide region complementary to said guide opening, the guide region being adapted be advanced into the guide opening in order to guide the actuating element on the base body.

7. The filling device as claimed in claim 6, wherein the actuating direction runs at an angle of substantially 90° to the longitudinal direction.

8. The filling device as claimed in claim 6, wherein the actuating element comprises a breaking structure, which, when the actuating element is advanced into the base body, moves into the cavity in such a way that it shatters an end region of an ampule held in the base body.

9. The filling device as claimed in claim 8, wherein the breaking structure, in the inserted state, projects substantially centrally into the cavity.

10. The filling device as claimed in claim 6,
wherein the actuating element comprises a breaking structure adapted to be advanced with one end into the cavity, and
wherein at this end an angular face, running obliquely to the actuating direction, is configured, in order to apply to an end region of an ampule held in the base body a shearing force acting at an angle to the longitudinal direction and at an angle to the actuating direction.

11. The filling device as claimed in claim 6, the device being configured to fill a single receptacle,
wherein the base body delimits precisely one cavity for the reception of precisely one ampule.

12. The filling device as claimed in claim 6,
wherein the base body additionally delimits at least a second cavity having a proximal end and a distal end,
wherein the base body is configured to receive at least a second ampule, at least by its distal end, sealingly in the second cavity, and
wherein the base body has a second removal opening, for removal of a fluid from the second cavity,
and wherein the first and the second cavity run substantially parallel to one another and define a common longitudinal direction.

13. The filling device as claimed in claim 12, wherein the actuating element comprises at least two mutually connected, parallelly arranged breaking structures, which are adapted be advanced into actuating openings of the base body along the actuating direction in order to shear off or shatter distal end regions of ampules disposed in the base body.

14. A combination of a filling device and a syringe, the filling device comprising a base body which forms at least a first cavity extending along a longitudinal direction and having a proximal end and a distal end, the base body being configured to receive an ampule, at least by its distal end, sealingly in the first cavity,
wherein the base body has a removal opening, for removal of a fluid from the cavity,
wherein the base body has a port, which communicates with the removal opening of the base body and is configured to interact with a complementary connecting piece of a receptacle,
and wherein the filling device additionally comprises an opening device, which is configured to open an ampule disposed in the first cavity,
the opening device comprising an actuating element which is adapted to be advanced into the base body along an actuating direction in order to shear off or shatter a distal end region of an ampule arranged in the base body, the actuating direction running at an angle to the longitudinal direction,
wherein an additional guide structure for the actuating element is configured on the base body, in order to guide the actuating element on the base body,
wherein the guide structure has a guide opening, and
wherein the actuating element has a guide region complementary to said guide opening, the guide region being adapted be advanced into the guide opening in order to guide the actuating element on the base body,
the syringe comprising:
at least a first syringe body having a cylindrical wall region, a cover wall, an outlet disposed in the cover wall, and a connecting piece communicating with the outlet;
at least a first syringe plunger, which is sealingly displaceable in the cylindrical wall region of the syringe body;
the connecting piece of the syringe body being connectable to said port of the base body.

15. A filling device for filling a receptacle with a fluid from at least one ampule,
the filling device comprising a base body which forms at least a first cavity extending along a longitudinal direction and having a proximal end and a distal end, the base body being configured to receive an ampule, at least by its distal end, sealingly in the first cavity, wherein the base body has a removal opening, for removal of a fluid from the cavity, wherein the base body has a port, which communicates with the removal opening of the base body and is configured to interact with a complementary connecting piece of a receptacle, and wherein the filling device additionally comprises an opening device, which is configured to open an ampule disposed in the first cavity, the opening device comprising an actuating element which is adapted to be advanced into the base body along an actuating direction in order to shear off or shatter a distal end region of an ampule arranged properly in the base body, the actuating direction running at an angle to the longitudinal direction, wherein the base body additionally delimits at least a second cavity having a proximal end and a distal end, wherein the base body is configured to receive at least a second ampule, at least by its distal end, sealingly in the second cavity, wherein the base body has a second removal opening, for removal of a fluid from the second cavity, wherein the first and the second cavity run substantially parallel to one another and define a common longitudinal direction, and wherein the actuating element comprises at least two mutually connected, parallelly arranged breaking structures, which are adapted be advanced into actuating openings of the base body along the actuating direction in order to shear off or shatter distal end regions of ampules disposed in the base body.

16. The filling device as claimed in claim 15, wherein the actuating direction runs at an angle of substantially 90° to the longitudinal direction.

17. The filling device as claimed in claim 15, wherein the at least two breaking structures, in the inserted state, project substantially centrally into the cavity.

18. The filling device as claimed in claim 15,
wherein each of the at least two breaking structures is adapted to be advanced with one respective end into the cavity, and wherein at each of these respective ends an angular face, running obliquely to the actuating direction, is configured, in order to apply to the respective end regions of the ampules held in the base body a shearing force acting at an angle to the longitudinal direction and at an angle to the actuating direction.

* * * * *